US012735461B2

(12) United States Patent
Bae et al.

(10) Patent No.: US 12,735,461 B2
(45) Date of Patent: Sep. 15, 2026

(54) SHEWANELLA ATLANTICA-DERIVED PROTEIN-EXPRESSING MICROORGANISM AND L-AMINO ACID PRODUCTION METHOD USING SAME

(71) Applicant: CJ CheilJedang Corporation, Seoul (KR)

(72) Inventors: Hyun Won Bae, Seoul (KR); Moo Young Jung, Seoul (KR); Sang Jun Kim, Seoul (KR); Sang Min Park, Seoul (KR); Hyo Jeong Byun, Seoul (KR); Yong Uk Shin, Seoul (KR); Han Hyoung Lee, Seoul (KR); Boram Lim, Seoul (KR); Jaewon Jang, Seoul (KR); Yunjung Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 283 days.

(21) Appl. No.: 17/916,528

(22) PCT Filed: Nov. 29, 2021

(86) PCT No.: PCT/KR2021/017793

§ 371 (c)(1),
(2) Date: Sep. 30, 2022

(87) PCT Pub. No.: WO2022/124670

PCT Pub. Date: Jun. 16, 2022

(65) Prior Publication Data

US 2025/0263446 A1 Aug. 21, 2025

(30) Foreign Application Priority Data

Dec. 9, 2020 (KR) ........................ 10-2020-0171739

(51) Int. Cl.

| | |
|---|---|
| ***C07K 14/195*** | (2006.01) |
| ***C12N 15/77*** | (2006.01) |
| ***C12P 13/06*** | (2006.01) |
| ***C12P 13/10*** | (2006.01) |

(52) U.S. Cl.

CPC ............ *C07K 14/195* (2013.01); *C12N 15/77* (2013.01); *C12P 13/06* (2013.01); *C12P 13/10* (2013.01)

(58) Field of Classification Search

CPC ....... C07K 14/195; C12N 15/77; C12P 13/06; C12P 13/10

See application file for complete search history.

(56) References Cited

U.S. PATENT DOCUMENTS

| | | |
|---|---|---|
| 7,629,142 B2 | 12/2009 | Ueda et al. |
| 2012/0015409 A1 | 1/2012 | Tabata et al. |

FOREIGN PATENT DOCUMENTS

| | | | |
|---|---|---|---|
| CN | 101243177 | 8/2008 | |
| CN | 110452856 | 11/2019 | |
| EP | 4261287 | 10/2023 | |
| JP | 2000-507086 | 6/2000 | |
| JP | 2005-237379 | 9/2005 | |
| JP | 2005-253459 | 9/2005 | |
| JP | 2005-278643 | 10/2005 | |
| KR | 10-0159812 | 8/1998 | |
| KR | 10-1999-0076708 | 10/1999 | |
| KR | 10-0786987 | 12/2007 | |
| KR | 10-0924065 | 10/2009 | |
| KR | 10-1126041 | 3/2012 | |
| KR | 10-2139806 | 7/2020 | |
| KR | 10-2770475 | 2/2025 | |
| RU | 2225883 | 3/2004 | |
| RU | 2316588 | 2/2008 | |
| WO | WO-2005073390 A2 * | 8/2005 | ............. C12P 13/08 |

OTHER PUBLICATIONS

Becker, et al. Systems and synthetic metabolic engineering for amino acid production—the heartbeat of industrial strain development, Current Opinion in Biotechnology, vol. 23, Issue 5, 2012, pp. 718-726, ISSN 0958-1669, https://doi.org/10.1016/j.copbio.2011.12.025. (Year: 2012).*

Reetz, MT. Laboratory evolution of stereoselective enzymes: a prolific source of catalysts for asymmetric reactions. Angew Chem Int Ed Engl. Jan. 3, 2011;50(1):138-74. doi: 10.1002/anie.201000826. PMID: 20715024. (Year: 2011).*

GenBank: RTR33311.1, amino acid transporter [Shewanella atlantica]. Direct submission by Yu, L. Submitted (Dec. 15, 2018) Key Laboratory of Marine Genetic Resources, Third Institute of Oceanography, State of Oceanic Administration, China. https://www.ncbi.nlm.nih.gov/protein/RTR33311.1 (Year: 2018).*

GenBank: RXNV01000002.1, Shewanella atlantica strain HAW-EB5 NODE_2_length_800876_cov_49.475599, wholegenome shotgun sequence. Direct submission by Yu, L. Submitted (Dec. 15, 2018) Key Laboratory of Marine Genetic Resources, China. pp. 1-2,42,213. https://www.ncbi.nlm.nih.gov/nuccore/RXNV01000002.1 (Year: 2018).*

Whisstock, James C., et al. “Prediction of protein function from protein sequence and structure.” Quarterly reviews of biophysics 36.3 (Aug. 2003): 307-340.

Witkowski, Andrzej, et al. “Conversion of a ß-ketoacyl synthase to a malonyl decarboxylase by replacement of the active-site cysteine with glutamine.” Biochemistry 38.36 (Aug. 18, 1999): 11643-11650.

Seffernick, Jennifer L., et al. “Melamine deaminase and atrazine chlorohydrolase: 98 percent identical but functionally different.” Journal of bacteriology 183.8 (Apr. 2001): 2405-2410.

Broun, Pierre, et al. “Catalytic plasticity of fatty acid modification enzymes underlying chemical diversity of plant lipids.” Science 282.5392 (Nov. 13, 1998): 1315-1317.

(Continued)

*Primary Examiner* — Melenie L Gordon
*Assistant Examiner* — Dennis Ignatius Armato, Jr.
(74) *Attorney, Agent, or Firm* — LEX IP MEISTER, PLLC

(57) ABSTRACT

Provided are a foreign protein-expressing microorganism and an L-amino acid production method using same. The foreign protein-expressing microorganism may have improved L-amino acid excretion and/or production capacity, compared to a wild type.

5 Claims, No Drawings

Specification includes a Sequence Listing.

(56) References Cited

OTHER PUBLICATIONS

Rospatent, Office Action of the corresponding Russian Patent Application No. 2022120185 dated Dec. 18, 2023.
Rospatent, a Patent Search Report of Russian Patent Application No. 2022120185 dated Dec. 18, 2023.
"A0A431WD72_9GAMM", [online], Internet, version t, UniProtKB, 2020: Accession: A0A431WD72,https://rest.uniprot.org/unisave/A0A431WD72?format=txt&version=6.
JPO, Office Action of JP 2022-554350 dated Aug. 29, 2023.
Anran Sun et al., "Efficient agmatine 1-10 C12P13/10 production using an arginine decarboxylase with substrate-specific activity", Journal of Chemical Technology and Biotechnology, vol. 92, No. 9, Feb. 21, 2017, pp. 2383-2391, XP093306603.
EPO, Search Report of EP 21903716.5 dated Sep. 15, 2025, total 44 pages.
NCBI Reference Sequence: WP_126504868.1, amino acid transporter [Shewanella atlantica], Dec. 28, 2018, total 1 page.
SIPO, Office Action of CN 202180016206.1 dated Feb. 26, 2026, total 10 pages.
KIPO, PCT Search Report & Written Opinion of PCT/KR2021/017793, dated Mar. 14, 2022.
NCBI, "Shewanella atlantica strain HAW-EB5 NODE_2_length_800876_cov_49.475599, whole genome shotgun sequence" GenBank accession No. RXNV01000002.1.
Rice, P., et al. "EMBOSS: The European Molecular Biology Open Software Suite", Trends in Genetics. vol. 16, No. 6, 276-277, Jun. 2000.
Needleman, Saul B., et al. "A General Method Applicable to the Search for Similarities in the Amino Acid Sequence of Two Proteins", Journal of molecular biology 48.3 (Mar. 1970): 443-453.
Devereux, J., et al. "A comprehensive set of sequence analysis programs for the VAX", Nucleic Acids Research 12. 1: 387-395, Jan. 1984.
Smith, Temple F., et al. "Comparison of biosequences." Advances in applied mathematics 2.4 (Dec. 1981): 482-489.
Gribskov, Michael, et al. "Sigma factors from *E. coli*, B. subtilis, phage SP01, and phage T4 are homologous proteins." Nucleic Acids Research 14.16 (Aug. 1986): 6745-6763.
Sambrook, J., et al. "Molecular cloning: a laboratory manual", No. Ed. 2. Cold spring harbor laboratory press, 1989, Exported Abstract.
Ausubel, F. M., et al. "Current Protocols in Molecular Biology", John Wiley & Sons, Inc., New York (1989).
Sambrook, J., et al. "Molecular cloning: a laboratory manual", No. Ed. 3, Cold spring harbor laboratory press, 2001, 9.50-9.51, 11.7-11.8.
Van der Rest, M. E., et al., "A heat shock following electroporation induces highly efficient transformation of Corynebacterium glutamicum with xenogeneic plasmid DNA", Applied Microbiology and Biotechnology 52.4 (Oct. 1999): 541-545.

* cited by examiner

SEQUENCE LISTING

```
<160> NUMBER OF SEQ ID NOS: 10

<210> SEQ ID NO 1
<211> LENGTH: 202
<212> TYPE: PRT
<213> ORGANISM: Artificial Sequence
<220> FEATURE:
<223> OTHER INFORMATION: Membrane protein derived from Shewanella
      atlantica (Sat)

<400> SEQUENCE: 1

Met Gln Ala Phe Ile Gln Gly Val Gly Ile Gly Gly Ser Leu Ile Met
1               5                   10                  15

Ala Val Gly Ala Gln Asn Ala Phe Val Leu Lys Gln Gly Leu Lys Arg
            20                  25                  30

Ser His Ser Leu Pro Ile Ala Gly Leu Cys Ser Leu Ile Asp Ala Leu
        35                  40                  45

Met Ile Thr Ala Gly Val Ala Gly Leu Gly His Leu Ile Leu Ala Phe
    50                  55                  60

Pro Leu Ile Lys Asp Ile Ala Ser Ile Gly Gly Ala Ile Phe Leu Leu
65                  70                  75                  80

Val Tyr Gly Ala Lys Ala Leu Arg Ser Ser Phe Asn Glu Gln Thr Ile
                85                  90                  95

Ser Gln Gly Ala Thr Lys Gly Thr Glu Thr Leu Lys Ala Ala Val Leu
            100                 105                 110

Thr Thr Leu Gly Ile Ser Leu Leu Asn Pro His Leu Tyr Leu Asp Thr
        115                 120                 125

Val Val Leu Leu Gly Ser Ile Ser Ala Gln Phe Glu Gly Val Asp Arg
    130                 135                 140

Pro Leu Phe Gly Ala Gly Ala Val Leu Ala Ser Phe Val Trp Phe Phe
```

-continued

```
145                 150                 155                 160

Ser Leu Ser Phe Gly Ala Arg Tyr Leu Ser Pro Leu Phe Gln Asn Pro
                165                 170                 175

Lys Ala Trp Ser Tyr Leu Asp Arg Phe Ile Cys Met Thr Met Trp Thr
            180                 185                 190

Ile Ala Ala Val Leu Leu Trp Pro Tyr Leu
        195                 200


<210> SEQ ID NO 2
<211> LENGTH: 609
<212> TYPE: DNA
<213> ORGANISM: Artificial Sequence
<220> FEATURE:
<223> OTHER INFORMATION: Sat coding nucleotide sequence

<400> SEQUENCE: 2

atgcaggcat ttattcaggg tgtaggaatt ggcggaagcc ttattatggc ggtgggcgca     60

caaaatgcgt ttgtattaaa gcaggggctg aagcgttcgc actctttacc cattgccgga    120

ctgtgttcat tgatcgatgc cttaatgata acggctggtg tggcaggcct gggtcatttg    180

attttggcct ttccattgat taaggatatt gccagtattg gtggggcgat cttcttgctg    240

gtttatggtg caaaggcttt aaggtcttcg tttaatgagc aaaccatatc tcaaggtgcg    300

acgaaaggga ctgaaaccct taaagctgcg gtgttgacaa ctttgggtat tagtttgctc    360

aacccgcatc tgtatctgga cacggttgtc ttgcttggta gcatcagtgc tcagtttgaa    420

ggtgttgacc gtcctctgtt tggcgcaggt gccgtactgg catcgtttgt gtggtttttt    480

agtttaagtt ttggtgcgag atacttaagt ccattatttc aaaaccctaa agcctggagc    540

tatttagaca ggtttatctg catgactatg tggaccattg cggcggtctt gttatggcct    600

tacttgtaa                                                            609


<210> SEQ ID NO 3
<211> LENGTH: 35
<212> TYPE: DNA
<213> ORGANISM: Artificial Sequence
<220> FEATURE:
<223> OTHER INFORMATION: Sat-F_primer

<400> SEQUENCE: 3

tagaggagac acaacatgca ggcatttatt caggg                                35


<210> SEQ ID NO 4
<211> LENGTH: 36
<212> TYPE: DNA
<213> ORGANISM: Artificial Sequence
<220> FEATURE:
<223> OTHER INFORMATION: Sat-R_primer

<400> SEQUENCE: 4

tagatgtcgg gcccattaca agtaaggcca taacaa                               36


<210> SEQ ID NO 5
<211> LENGTH: 35
<212> TYPE: DNA
<213> ORGANISM: Artificial Sequence
<220> FEATURE:
<223> OTHER INFORMATION: PgapA-F_primer

<400> SEQUENCE: 5

aatgagttcc tcgagaaacg accgagccta ttggg                                35
```

-continued

<210> SEQ ID NO 6
<211> LENGTH: 35
<212> TYPE: DNA
<213> ORGANISM: Artificial Sequence
<220> FEATURE:
<223> OTHER INFORMATION: PgapA-R_primer

<400> SEQUENCE: 6
taaatgcctg catgttgtgt ctcctctaaa gattg 35

<210> SEQ ID NO 7
<211> LENGTH: 20
<212> TYPE: DNA
<213> ORGANISM: Artificial Sequence
<220> FEATURE:
<223> OTHER INFORMATION: pDZTn-1_primer

<400> SEQUENCE: 7
acgacgctgg tatttctccc 20

<210> SEQ ID NO 8
<211> LENGTH: 20
<212> TYPE: DNA
<213> ORGANISM: Artificial Sequence
<220> FEATURE:
<223> OTHER INFORMATION: pDZTn-2_primer

<400> SEQUENCE: 8
tgattgtcga tatgaccggg 20

<210> SEQ ID NO 9
<211> LENGTH: 20
<212> TYPE: DNA
<213> ORGANISM: Artificial Sequence
<220> FEATURE:
<223> OTHER INFORMATION: Tn-1_primer

<400> SEQUENCE: 9
taaggcaccg cagaatgtag 20

<210> SEQ ID NO 10
<211> LENGTH: 20
<212> TYPE: DNA
<213> ORGANISM: Artificial Sequence
<220> FEATURE:
<223> OTHER INFORMATION: Tn-2_primer

<400> SEQUENCE: 10
taggactcac catcaccggc 20

SHEWANELLA ATLANTICA-DERIVED PROTEIN-EXPRESSING MICROORGANISM AND L-AMINO ACID PRODUCTION METHOD USING SAME

TECHNICAL FIELD

A microorganism expressing a foreign protein and a method for producing L-amino acid using thereof are provided. The microorganism expressing a foreign protein may have improved L-amino acid exporting ability and/or productivity compared to the wild type.

BACKGROUND ART

A Genus *Corynebacterium* microorganism is a gram-positive microorganism that is widely used in production of L-amino acid. L-amino acid is used in animal feed, human pharmaceutical and cosmetic industries and is produced by fermentation using a *Corynebacterium* strain.

Many attempts have been made to improve the method for production of L-amino acid using a *Corynebacterium* strain. Among them, there have been studies to improve a *Corynebacterium* strain producing L-amino acid by destroying a specific gene or attenuating expression using recombinant DNA technology. In addition, there have been studies to study the effect on L-amino acid production by amplifying a gene involved in biosynthesis of each L-amino acid and to improve a *Corynebacterium* strain producing L-amino acid. Nevertheless, there is still a need to develop a strain with improved productivity of L-amino acid.

DISCLOSURE

Technical Problem

One example provides a microorganism expressing a foreign protein. The foreign protein is a protein derived from a heterogeneous microorganism of the microorganism, and may be a protein whose lysine exporting function is newly discovered in the present description. The microorganism expressing a foreign protein may have improved exporting ability and/or productivity of L-amino acid, compared to a homogenous microorganism which does not express the foreign protein.

Another example provides a composition for producing L-amino acid comprising the microorganism expressing a foreign protein.

Other example provides a method for production of L-amino acid, comprising culturing the microorganism expressing a foreign protein.

The microorganism may be a Genus *Corynebacterium* microorganism.

Technical Solution

In the present description, for the purpose of increasing the L-amino acid productivity of a Genus *Corynebacterium* microorganism, it was attempted to improve the strain by searching for and introducing a novel exporting protein of L-amino acid. Described using L-lysine as a representative example, in general, there is a method of improving the L-lysine yield of the strain or increasing the L-lysine product quantity per hour in order to increase the lysine productivity. The L-lysine exporting protein is a membrane protein exporting lysine produced thorough biosynthesis, and the improvement of this protein is important for increasing the lysine yield and productivity. However, the increase in the expression level of the L-lysine exporting protein (lysE, Ncgl1214) possessed by the Genus *Corynebacterium* microorganism has a limit in improving the lysine productivity.

Accordingly, in the present description, a new foreign L-amino acid exporting protein with high L-amino acid exporting activity was searched, and by introducing this to a lysine producing strain, a recombinant strain with improved L-amino acid exporting ability and/or productivity was provided.

In the present description, as a representative example of the new foreign L-amino acid exporting protein, a novel L-amino acid exporting protein derived from *Shewanella atlantica* and a gene encoding this were discovered, and as the result of expressing this to a microorganism producing L-amino acid, it was confirmed that the exporting ability/productivity of L-amino acid was significantly improved, compared to a microorganism in which the gene was not expressed.

One example provides a microorganism expressing a foreign protein. The foreign protein is a protein derived from a heterogeneous microorganism to the microorganism, and may be a protein whose lysine exporting function was newly discovered. The microorganism expressing a foreign protein may have improved exporting ability and/or productivity of L-amino acid, for example, L-lysine or L-arginine.

Another example provides a composition for production of L-amino acid comprising the microorganism expressing a foreign protein.

Other example provides a method for production of L-amino acid, comprising culturing the microorganism expressing a foreign protein.

The microorganism may be a Genus *Corynebacterium* microorganism.

The L-amino acid may comprise L-lysine or L-arginine.

Hereinafter, it will be described in more detail.

In the present description, the foreign protein may be a protein derived from a microorganism belonging to a different genus from the parent strain (microorganism before mutation) or a different species of microorganism, and for example, it may be a membrane protein derived from a microorganism other than a microorganism belonging to the genus *Corynebacterium*, which is a protein having the exporting ability of L-lysine or L-arginine, newly discovered in the present description. In one example, the foreign protein may be a membrane protein derived from a genus *Shewanella* microorganism, for example, *Shewanella atlantica* (for example, represented by the amino acid sequence of SEQ ID NO: 1); a protein (e.g., membrane protein) having a sequence identity or homology of 60% or more, 70% or more, 75% or more, 80% or more, 85% or more, 90% or more, 91% or more, 92% or more, 93% or more, 94% or more, 95% or more, 96% or more, 97% or more, 98% or more, 99% or more, 99.5% or more, or 99.9% or more to the protein.

The microorganism may comprise or express one or more kinds of the foreign protein. The microorganism expressing a foreign protein may be a recombinant microorganism in which a polynucleotide encoding the foreign protein described above is introduced. In one example, the polynucleotide encoding the protein of SEQ ID NO: 1 may be represented by the nucleic acid sequence of SEQ ID NO: 2 or a sequence having a sequence identity or homology of 60% or more, 70% or more, 75% or more, 80% or more, 85% or more, 90% or more, 91% or more, 92% or more, 93% or more, 94% or more, 95% or more, 96% or more, 97% or more, 98% or more, 99% or more, 99.5% or more, or 99.9% or more with the nucleic acid sequence of SEQ ID NO: 2.

The microorganism expressing a foreign protein may be a microorganism producing L-amino acid having the L-amino acid exporting ability and/or productivity.

In the present description, the term "L-amino acid producing microorganism" may be used to mean the case that the microorganism has the increased L-amino acid exporting ability and/or productivity as the microorganism having the L-amino acid exporting ability and/or productivity is mutated to express a foreign protein as described above and/or the microorganism has the L-amino acid exporting ability and/or productivity as a microorganism not having the L-amino acid exporting ability and/or productivity is mutated to express the foreign protein. In the present description, "microorganism" encompasses single-celled bacteria, and may be used interchangeably with "cell". In the present description, in order to distinguish the microorganism before being mutated to express the foreign protein from the mutated microorganism, it may be expressed as a "parent microorganism (or parent strain) or host cell".

The L-amino acid may be L-lysine or L-arginine, for example, L-lysine.

In one example, the microorganism may be selected from all microorganisms having the L-amino acid exporting ability and/or productivity. In one example, the microorganism, for example, parent strain before mutation may be (1) a microorganism having L-amino acid exporting ability and/or productivity naturally, or (2) a microorganism having L-amino acid exporting ability and/or productivity or with improved L-amino acid exporting ability and/or productivity, as mutation is introduced to the microorganism having L-amino acid exporting ability and/or productivity naturally or a strain having significantly low L-amino acid exporting ability and/or productivity.

In one specific example, the microorganism may be one or more kinds selected from the group consisting of (1) a microorganism having L-amino acid exporting ability and/or productivity naturally or (2) all the genus *Corynebacterium* microorganisms having L-amino acid exporting ability and/or productivity or with improved L-amino acid exporting ability and/or productivity, as mutation is introduced to the microorganism having L-amino acid exporting ability and/or productivity naturally or a strain having significantly low L-amino acid exporting ability and/or productivity. The genus *Corynebacterium* microorganism may include *Corynebacterium glutamicum, Corynebacterium ammoniagenes, Brevibacterium lactofermentum, Brevibacterium flavum, Corynebacterium thermoaminogenes, Corynebacterium efficiens*, and the like, but not definitely limited thereto. Much more specifically, the genus *Corynebacterium* microorganism may be *Corynebacterium glutamicum.*

In one example, the microorganism expressing a foreign protein may be a microorganism in which mutation to express the foreign protein is introduced. As such, the microorganism mutated to express the foreign protein, may have increased L-amino acid exporting ability and/or productivity, compared to a homogeneous non-modified microorganism. The non-modified microorganism is a microorganism which does not express the foreign protein, and may mean a homogeneous microorganism in which mutation to express the foreign protein is not introduced or a microorganism before introducing the mutation.

In the present description, "mutation to express a foreign protein" may mean all manipulations that allow a parent strain to express the foreign protein described above. In one example, the mutation to express a foreign protein may introduce a polynucleotide encoding the foreign protein or a recombinant vector comprising the same into the parent strain.

The "microorganism in which mutation to express a foreign protein is introduced" or "microorganism mutated to express a foreign protein" may be a microorganism in which a polynucleotide encoding the foreign protein or a recombinant vector comprising the same is introduced, and compared to the non-modified microorganism, the L-amino acid exporting ability and/or productivity are imparted or increased.

In one example, the parent strain may be wild type or mutated so that the exporting ability and/or productivity of L-amino acid are increased, for example, the protein activity involved in biosynthesis or metabolism of L-amino acid is controlled (increased (promoted) or reduced (inhibited)), compared to the wild type, but not limited thereto.

In one specific example, the microorganism producing L-amino acid in which the foreign protein is expressed may be accession number KCCM_12828P.

In the present description, that a polynucleotide (which may be used interchangeably with "gene") or a polypeptide (which may be used interchangeably with "protein") "comprises a specific nucleic acid sequence or an amino acid sequence, consists of a specific nucleic acid sequence or an amino acid sequence, or is represented by a specific nucleic acid sequence or an amino acid sequence" is an interchangeable expression with the equivalent meaning, and may mean that the polynucleotide or polypeptide necessarily comprises the specific nucleic acid sequence or amino acid sequence, and may be interpreted as comprising a "substantially equivalent sequence" in which a mutation (deletion, substitution, modification and/or addition) is added to the specific nucleic acid sequence or amino acid sequence within the range of maintaining the original function and/or desired function of the polynucleotide or polypeptide (or not excluding the mutation).

In one example, the nucleic acid sequence or amino acid sequence provided in the present description may comprise that modified by common mutagenesis, for example, direct evolution and/or site-directed mutagenesis, and the like, within the range of maintaining its original function and/or desired function. In the present description, unless otherwise described, that a polynucleotide or polypeptide "comprises a specific nucleic acid sequence or amino acid sequence or consists of the sequence" may mean that the polynucleotide or polypeptide (i) necessarily comprises the specific nucleic acid sequence or amino acid sequence, or (ii) consists of the amino acid sequence having a homology of 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more, 99.5% or more, or 99.9% or more to the specific nucleic acid sequence or amino acid sequence and maintains the original function and/or desired function. In the present description, the original function may be lysine exporting protein function (in case of amino acid sequence) or function encoding a protein having the lysine exporting protein function (in case of nucleic acid sequence), and the desired function may mean function to increase or give the exporting ability and/or productivity of L-amino acid (for example, L-lysine, L-arginine or a combination thereof) of a microorganism.

Herein, the term 'homology' or 'identity' means a degree related to two given amino acid sequences or nucleotide sequences and may be expressed as a percentage. The terms homology and identity are often used interchangeably.

The sequence homology or identity of the conserved polynucleotide or polypeptide is determined by a standard arrangement algorithm, and a default gap penalty established by a program to be used. Substantially, a homologous or identical sequence may be hybridized under moderate or high stringent conditions along the entire sequence or at least about 50%, 60%, 70%, 80% or 90% of the full-length. It is apparent that hybridization comprises polynucleotides containing common codons or codons considering codon degeneracy in polynucleotides.

Whether any two polynucleotide or polypeptide sequences have homology, similarity or identity, may be determined using a known computer algorithm such as "FASTA" program, for example, using a default parameter as Pearson et al (1988) [Proc. Natl. Acad. Sci. USA 85]: 2444. Otherwise, it may be determined using Needleman-Wunsch algorithm (Needleman and Wunsch, 1970, J. Mol. Biol. 48:443-453), as performed in Needleman program of EMBOSS package (EMBOSS: The European Molecular Biology Open Software Suite, Rice et al., 2000, Trends Genet. 16:276-277) (version 5.0.0 or later version) (including GCG program package (Devereux, J., et al, Nucleic Acids Research 12:387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48:1073). For example, using BLAST, or ClustalW of National Center for Biotechnology Information Database, the homology, similarity or identity may be determined.

The homology, similarity or identity of the polynucleotide or polypeptide may be determined by comparing the sequence information, as known in Smith and Waterman, Adv. Appl. Math (1981) 2:482, for example, using GAP computer program such as Needleman et al. (1970), J Mol Biol. 48:443. In summary, the GAP program may be defined as a value of dividing the total number of symbols in the shorter of two sequences by the number of similarly arranged symbols (namely, nucleotides or amino acids). The default parameter for the GAP program may include (1) a binary system comparison matrix (containing a value of 1 for identity and 0 for non-identity) and an aggravated comparison matrix of Gribskov et al (1986) Nucl. Acids Res. 14:6745, described by Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or a gap opening penalty 10, a gap extension penalty 0.5); and (3) no penalty for an end gap.

In addition, whether any two polynucleotide or polypeptide sequences have homology, similarity or identity may be confirmed by comparing sequences by a southern hybridization experiment under defined stringent conditions, and the defined appropriate hybridization condition may be determined by a method known to those skilled in the art, within the range of the corresponding technology (for example, J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York). The nucleic acid sequence described in the present description may have various modifications in a coding region within the range that does not change the amino acid sequence and/or function of a protein expressed from the coding region, in consideration of a preferred codon in a microorganism to express the protein (lysine exporting protein) due to degeneracy of the codon.

In one example, the polynucleotide comprising a specific nucleic acid sequence provided in the present description may be interpreted to comprise not only the specific nucleic acid sequence or substantially equivalent nucleic acid sequence thereto, but also a polynucleotide fragment comprising a complementary nucleic acid sequence to the specific nucleic acid sequence. Specifically, the polynucleotide having complementarity may be hybridized at a Tm value appropriately adjustable by those skilled in the art on purposes, for example a Tm value of 55° C., 60° C., 63° C. or 65° C., and analyzed under the condition described below: This condition is described specifically in the known literature. For example, a condition in which genes having high complementarity of 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 98% or more, 99.5% or more, or 99.9% or more are hybridized and genes having lower complementarity are not hybridized, or a common washing condition of southern hybridization, which is a condition of washing once, specifically, twice to 3 times, at the salt concentration and temperature corresponding to 60° C., 1×SSC (saline-sodium citrate buffer), and 0.1% (w/v) SDS (Sodium Dodecyl Sulfate); 60° C., 0.1×SSC, and 0.1% SDS; or 68° C., 0.1×SSC, and 0.1% SDS, or the like, but not limited thereto. In the hybridization, it may be required that two nucleotides have a complementary sequence, or a mismatch between bases may be allowed according to the severity level of hybridization. The term "complementary" may be used to describe the relationship between nucleotide bases capable of hybridizing with each other. For example, in case of DNA, adenosine is complementary to thymine and cytosine is complementary to guanine. The appropriate severity level of hybridizing polynucleotides is dependent on the length of polynucleotides and degree of complementarity, and this is well known to the related technical field (See Sambrook et al., supra, 9.50-9.51, 11.7-11.8).

The introduction of the polynucleotide or vector may be performed by selecting a known transformation method by those skilled in the art. In the present description, the term "transformation" means introducing a polynucleotide encoding a target protein (foreign protein) or a vector comprising the same into a host cell to express a protein encoded by the polynucleotide in the host cell. As long as it can be expressed in the host cell, whether inserted and located in the chromosome of the host cell or located extrachromosomally, the transformed polynucleotide may include all of them. In addition, the polynucleotide includes DNA and/or RNA encoding a target protein. As long as the polynucleotide is introduced and expressed in a host cell, the form in which it is introduced is not limited. For example, the polynucleotide may be introduced into a host cell in a form of an expression cassette which is a gene structure comprising all elements required to be expressed by itself. The expression cassette may generally comprise regulatory elements such as a promoter which is operably linked to the polynucleotide, a transcription termination signal, a ribosome binding site and/or a translation termination signal, and the like. The expression cassette may be in a form of an expression vector capable of self-replication. In addition, the polynucleotide may be introduced into a host cell in its own form and operably linked to a sequence required for expression in the host cell. In the above, the term "operably connected" may mean that expression regulatory elements (e.g., promoter) and the polynucleotide are functionally linked in order that the expression regulatory elements perform regulation of transcription (e.g., transcription initiation) of the polynucleotide encoding a target protein (foreign protein). Operable linking may be performed using a genetic recombination technique known in the art, and for example, may be performed by conventional site-specific DNA cleavage and ligation, but is not limited thereto.

The method for transforming the polynucleotide into a host cell may be performed by any method of introducing a nucleic acid into a cell (microorganism), and may be performed by appropriately selecting a transformation technique known in the art according to the host cell. As the known transformation method, electroporation, calcium phosphate ($CaPO_4$) precipitation, calcium chloride ($CaCl_2$)) precipitation, microinjection, polyethylene glycol (PEG) precipitation (polyethylene glycol-mediated uptake), DEAE-dextran method, cation liposome method, lipofection, lithium acetate-DMSO method, and the like may be illustrated, but not limited thereto.

The introduction (insertion) into a host cell genome (chromosome) of the polynucleotide may be performed by appropriately selecting a known method by those skilled in the art, and for example, may be performed using an RNA-guided endonuclease system (or CRISPR system; for example, one or more selected from the group consisting of (a) an RNA-guided endonuclease (e.g., Cas9 protein, etc.), its encoding gene, or a vector comprising the gene; and (b) a mixture comprising a guide RNA (e.g., single guide RNA (sgRNA), etc.), its encoding DNA, or a vector comprising the DNA (for example, a mixture of a RNA-guided endonuclease protein and a guide RNA, etc.), a complex (for example, ribonucleic acid fusion protein (RNP), a recombinant vector (For example, a vector comprising an RNA-guided endonuclease encoding gene and a guide RNA encoding DNA together, etc.)), but not limited thereto.

Herein, the term "vector" means a DNA product containing the nucleotide sequence of a polynucleotide encoding the target protein operably linked to a suitable regulatory sequence so as to express the target protein in a suitable host. The regulatory sequence may comprise a promoter capable of initiating transcription, any operator sequence for regulating transcription, a sequence encoding a suitable mRNA ribosome binding site, and/or a sequence regulating termination of transcription and/or translation. The vector may be expressed independently of the genome of the host cell or may be integrated into the genome of the host cell, after transformation into an appropriate host cell.

The vector usable herein is not particularly limited as long as it is capable of replicating in a host cell, and may be selected from all commonly used vectors. The example of the commonly used vector may include natural or recombinant plasmids, cosmids, viruses, bacteriophages, and the like. For example, for the vector, as a phage vector or cosmid vector, pWE15, M13, MBL3, MBL4, IXII, ASHII, APII, t10, t11, Charon4A, and Charon21A, and the like may be used, and as a plasmid vector, pBR-based, pUC-based, pBluescriptII-based, pGEM-based, pTZ-based, pCL-based and pET-based, and the like, may be used. Specifically, pDZ, pACYC177, pACYC184, pCL, pECCG117, pUC19, pBR322, pMW118, pCC1BAC vectors, and the like may be illustrated, but not limited thereto.

The vector usable herein may be a known expression vector and/or a vector for insertion into a host cell chromosome of a polynucleotide. The insertion into a host cell chromosome of a polynucleotide may be conducted by any method known in the art, for example, homologous recombination or CRISPR system, but not limited thereto. The vector may further comprise a selection marker to confirm insertion into the chromosome. The selection marker is to select a transformed cell by the vector, that is, to confirm insertion of the polynucleotide, and it may be selected among genes giving selectable phenotypes such as drug resistance, auxotrophic requirement, resistance to cytotoxic agents, or expression of a surface protein and used. As only the cells expressing the selection marker are survived or exhibit other expression traits in an environment treated with a selective agent, transformed cells may be selected.

Other example provides a method for increasing L-amino acid exporting activity and/or productivity of the microorganism or a method for giving L-amino acid exporting activity and/or productivity to the microorganism, comprising introducing (transforming) the aforementioned foreign protein, its encoding polynucleotide or a recombinant vector comprising the polynucleotide into a microorganism is provided.

The foreign protein, polynucleotide and microorganism are same as described above.

Other example provides a method for production of L-amino acid, comprising culturing the aforementioned L-amino acid producing microorganism in a medium. The method may further comprise recovering L-amino acid from the cultured microorganism, medium or both of them, after the culturing.

In the method, the culturing the microorganism may be performed by a known batch culturing method, a continuous culturing method, a fed-batch culturing method, and the like, but not particularly limited thereto. Then, the culturing condition, is not particularly limited thereto, but the optimal pH (for example, pH 5 to 9, specifically, pH 6 to 8, most specifically, pH 6.8) may be adjusted using a basic compound (e.g.: sodium hydroxide, potassium hydroxide or ammonia) or an acidic compound (e.g.: phosphoric acid or sulfuric acid), and the aerobic condition may be maintained by introducing oxygen or an oxygen-containing gas mixture to a culture. The culturing temperature may be maintained at 20 to 45° C., or 25 to 40° C., and it may be cultured for about 10 to 160 hours, but not limited thereto. The L-amino acid produced by the culturing may be secreted to a medium or remain in cells.

The medium usable in the culturing may individually use one or more kinds selected from the group consisting of sugar and carbohydrate (e.g.: glucose, sucrose, lactose, fructose, maltose, molasse, starch and cellulose), oil and fat (e.g.: soybean oil, sunflower oil, peanut oil and coconut oil), fatty acid (e.g.: palmitic acid, stearic acid and linoleic acid), alcohol (e.g.: glycerol and ethanol), organic acid (e.g.: acetic acid), and the like, or mix and use two kinds or more of them, as a carbon source, but not limited thereto. As a nitrogen source, one or more kinds selected from the group consisting of nitrogen-containing organic compounds (e.g.: peptone, yeast extract, meet juice, malt extract, corn steep liquid, soybean flower and urea), inorganic compounds (e.g.: ammonium sulfate, ammonium chloride, ammonium phosphate, ammonium carbonate and ammonium nitrate), and the like may be used individually or in a mixture of two or more of them, but not limited thereto. As a phosphorus source, one or more kinds selected from the group consisting of potassium dihydrogen phosphate, dipotassium hydrogen phosphate, sodium-containing salts corresponding thereto, and the like may be used individually or in a mixture of two or more of them, but not limited thereto. In addition, the medium may comprise an essential growth promoting substance such as other metal salts (e.g.: magnesium sulfate or iron sulfate), amino acid and/or vitamins.

The recovering L-amino acid may be collecting desired amino acid from a medium, culture solution or microorganism, using a known appropriate method in the art according to the culturing method. For example, the revering may be performed by one or more methods selected from centrifugation, filtering, anion exchange chromatography, crystallization, HPLC, and the like. The method for recovering L-amino acid may additionally comprise purification before, simultaneously, or after that.

Advantageous Effects

In the present description, a technology increasing exporting ability and/or productivity of L-amino acid of a microorganism is provided, and for this, a foreign protein whose exporting ability of L-amino acid is newly discovered, and a technology capable of improving productivity of L-amino acid compared to a parent strain, by introducing the foreign protein to a microorganism are provided.

MODE FOR INVENTION

Hereinafter, the present invention will be described in more detail by examples, but they are illustrative only, and are not intended to limit the scope of the present invention. It is apparent to those skilled in the art that the examples described below may be modified without departing from the essential gist of the invention.

Example 1: L-Lysine Exporting Gene Search and Selection

In order to search an exporting gene with high L-lysine exporting activity compared to a L-lysine exporter (lysE, Ncgl1214) inherently possessed by a Genus *Corynebacterium* microorganism, RPS-BLAST searching using NCBI CDD (Common Domain Database) and BLAST searching using KEGG Protein Database were performed. Candidate proteins considered as membrane proteins capable of exporting L-lysine were selected.

TABLE 1

L-lysine exporting membrane protein candidate group

| No. | Strain | Protein registration number | Genome registration number |
|---|---|---|---|
| 1 | *Shewanella oneidensis* MR-1 | WP_011072781.1 | NC_004347.2 |
| 2 | *Corynebacterium glutamicum* ATCC13032 | WP_003854734.1 | NC_003450.3 |
| 3 | *Aeromonas allosaccharophila* | WP_042063605.1 | NZ_CDCB01000123 |
| 4 | *Bacillus pseudofirmus* OF4 | WP_012958260.1 | NC_013791.2 |
| 5 | *Bacillus halodurans* C-125 | WP_010899078.1 | NC_002570.2 |
| 6 | *Natrialba aegyptia* | WP_006666837.1 | NZ_AOIP01000039.1 |
| 7 | *Haloquadratum walsbyi* | WP_011571763.1 | NC_008212.1 |
| 8 | *Thermotoga maritima* MSB8 | WP_004083139.1 | NC_000853.1 |
| 9 | *Pyrodictium delaneyi* | WP_055407773.1 | NZ_CP013011.1 |
| 10 | *Bacteroides coprophilus* | WP_008140089.1 | NZ_EQ973631.1 |
| 11 | *Shewanella atlantica* HAW-EB5 | WP_126504868.1 | NZ_RXNV01000002.1 |

Example 2: Production of Foreign Membrane Protein Gene-Introduced Vector

The membrane protein derived from *Shewanella atlantica* (Sat) selected in Example 1 has the amino acid sequence of SEQ ID NO: 1 The information (accession number NZ_RXNV01000002.1) of genes encoding the membrane protein and surrounding nucleic acid sequences was obtained from U.S. National Institutes of Health (NIH GenBank). DNA synthesis was performed, based on the corresponding gene sequence (Cosmo genetech, Korea). To amplify genes, PCR (Solg™ Pfu-X DNA polymerase) was performed using the synthesized DNA as a template and primers (Table 2) of SEQ ID NOs: 3 and 4 (Table 3). As a result, a gene fragment of 639 bp including the gene (SEQ ID NO: 2) of 609 bp was obtained.

TABLE 2

Primer sequence

| No. | Name | DNA sequence (5'→3') |
|---|---|---|
| SEQ ID NO: 3 | Sat-F | TAGAGGAGACACAACATGCA GGCATTTATTCAGGG |
| SEQ ID NO: 4 | Sat-R | TAGATGTCGGGCCCATTACA AGTAAGGCCATAACAA |
| SEQ ID NO: 5 | PgapA-F | AATGAGTTCCTCGAGAAACG ACCGAGCCTATTGGG |
| SEQ ID NO: 6 | PgapA-R | TAAATGCCTGCATGTTGTGT CTCCTCTAAAGATTG |
| SEQ ID NO: 7 | pDZTn-1 | ACGACGCTGGTATTTCTCCC |
| SEQ ID NO: 8 | pDZTn-2 | TGATTGTCGATATGACCGGG |

TABLE 3

PCR performance condition

| Stage | Temperature | Time |
|---|---|---|
| Initialization | 95° C. | 2 minutes |
| Denaturation | 95° C. | 20 seconds |
| Annealing | 62° C. | 40 seconds |
| Elongation | 72° C. | 0.5~1 minute |
| Post Elongation | 72° C. | 5 minutes |

To secure the gapA promoter derived from *Corynebacterium glutamicum*, PCR (Solg™ Pfu-X DNA polymerase) was performed using genomic DNA of *Corynebacterium glutamicum* ATCC 13032 as a template and primers (Table 2) of SEQ ID NOs: 5 and 6 (Table 3). The amplified gapA promoter site and the obtained *Shewanella atlantica*-derived gene fragment and the vector pDZTn cut with NdeI restriction enzyme (Korean Patent No. 10-1126041) were connected using Gibson Assembly (DG Gibson et al., NATURE METHODS, VOL. 6 NO. 5, May 2009, NEBuilder HiFi DNA Assembly Master Mix) method, and then transformed to *E. coli* DH5α, and smeared in a LB solid medium including kanamycin (25 mg/l). To select a colony transformed with the vector in which the desired gene and pDZTn were connected, PCR was performed using primers of SEQ ID NOs: 7 and 8. A plasmid was obtained using a commonly known plasmid extraction method from the selected colony, and this plasmid was named pDZTn-PgapA-Sat.

Example 3: Production of Foreign Membrane Protein-Introduced Strain

After transforming *Corynebacterium glutamicum* KCCM11016P strain producing L-lysine (Korean Patent No. 10-0159812) using the produced pDZTn-PgapA-Sat vector by electroporation (Appl. Microbiol. Biotechnol. (1999) 52:541-545), through a secondary cross process, a strain in which PgapA-Sat was inserted between the transposon genes was obtained. Using primers (Table 4) of SEQ ID NO: 9 and SEQ ID NO: 10 capable of amplifying adjacent sites including the position in which the corresponding gene was inserted, PCR and sequencing were performed, and the corresponding gene manipulation was confirmed. The strain obtained in this way was named *Corynebacterium glutamicum* KCCM11016P::PgapA-Sat.

TABLE 4

| Primer sequence | | |
|---|---|---|
| No. | Name | DNA sequence |
| SEQ ID NO: 9 | Tn-1 | TAAGGCACCGCAGAATGTAG |
| SEQ ID NO: 10 | Tn-2 | TAGGACTCACCATCACCGGC |

Example 4: Comparison of L-Amino Acid Productivity in Foreign Membrane Protein-Introduced KCCM11016P Strain The microbial cell amount, glucose consumption ability and amino acid productivity were compared, by culturing the KCCM11016P::PgapA-Sat strain and the control group KCCM11016P by the following method.

At first, each strain was inoculated in a 250 ml corner-baffled flask containing a 25 ml seed medium, and cultured with shaking at 30° C. for 20 hours at 200 rpm. The seed culture solution of 1 ml was inoculated in a 250 ml corner-baffled flask containing a 24 ml production medium, and cultured with shaking at 37° C. for 42 hours at 200 rpm.

After the end of culturing, the yield of L-amino acid was measured by HPLC. The experiment was repeated 3 times, and the culture result (average value) was shown in Table 5.

<Seed Medium (pH 7.0)>

Glucose 20 g, peptone 10 g, yeast extract 5 g, urea 1.5 g, $KH_2PO_4$ 4 g, $K_2HPO_4$ 8 g, $MgSO_4 \cdot 7H_2O$ 0.5 g, biotin 0.1 mg, thiamine HCl 1 mg, calcium-pantothenic acid 22 mg, nicotinamide 2 mg (based on distilled water 1 liter)

<Production Medium (pH 7.0)>

Glucose 45 g, $(NH_4)_2SO_4$ 15 g, soybean protein 10 g, molasse 10 g, $KH_2PO_4$ 0.55 g, $MgSO_4 \cdot 7H_2O$ 0.6 g, biotin 0.9 mg, thiamine hydrochloride 4.5 mg, calcium-pantothenic acid 4.5 mg, nicotinamide 30 mg, $MnSO_4$ 9 mg, $FeSO_4$ 9 mg, $ZnSO_4$ 0.45 mg, $CuSO_4$ 0.45 mg, $CaCO_3$ 30 g (based on distilled water 1 liter).

TABLE 5

L-amino acid productivity comparison (KCCM11016P)

| Strain | $OD_{562}$ | Consumed glucose (g/L) | Lysine concentration (g/L) | Arginine concentration (mg/L) |
|---|---|---|---|---|
| KCCM11016P | 51 | 50 | 12.1 | 24.2 |
| KCCM11016P::PgapA-Sat | 40.5 | 50 | 13.2 | 26.8 |

The KCCM11016P::PgapA-Sat strain (*Corynebacterium glutamicum* CA03-1486) was internationally deposited to Korean Culture Center of Microorganisms (KCCM), an international depository authority under the Budapest Treaty on Oct. 29, 2020 and was given an accession number as KCCM 12828P.

Example 5: Comparison of L-Amino Acid Productivity in Foreign Membrane Protein-Introduced KCCM10770P Strain A strain in which PgapA-Sat gene was inserted on the transposon position on the genome of *Corynebacterium glutamicum* KCCM10770P (Korean Patent No. 10-0924065) strain was obtained using the method described in Example 3. The strain obtained in this way was named *Corynebacterium glutamicum* KCCM10770P::PgapA-Sat.

By culturing the KCCM10770P::PgapA-Sat strain and the control group KCCM10770P, the microbial cell amount, glucose consumption ability and amino acid productivity were compared (See Example 4 for evaluation method). The experiment was repeated 3 times, and the culture result (average value) was shown in Table 6.

TABLE 6

L-amino acid productivity comparison (KCCM10770P)

| Strain | $OD_{562}$ | Consume glucose (g/L) | Lysine yield (g/L) | Arginine concentration (mg/L) |
|---|---|---|---|---|
| KCCM10770P | 70.3 | 50 | 8.3 | 16.6 |
| KCCM10770P::PgapA-Sat | 58.8 | 50 | 9.8 | 20.1 |

As shown in Table 6, the KCCM10770P::PgapA-Sat strain showed the increased amino acid productivity compared to the control strain KCCM10770P.

Example 6: Comparison of L-Amino Acid Productivity in Foreign Membrane Protein-Introduced CJ3P Strain A strain in which PgapA-Sat gene was inserted was obtained using the method described in Example 3 on the transposon position on the genome of the *Corynebacterium glutamicum* CJ3P (U.S. Pat. No. 9,556,463 B2) strain having the L-lysine productivity by introducing 3 kinds of mutants [pyc(P458S), hom(V59A), lysC(T311I)] into a wild type strain. The strain obtained in this way was named *Corynebacterium glutamicum* CJ3P::PgapA-Sat.

By culturing the CJ3P::PgapA-Sat strain and the control group CJ3P, the microbial cell amount, glucose consumption ability and amino acid productivity were compared (See Example 4 for evaluation method). The experiment was repeated 3 times, and the culture result (average value) was shown in Table 7.

TABLE 7

L-amino acid productivity comparison (CJ3P)

| Strain | $OD_{562}$ | Consume glucose (g/L) | Lysine yield (g/L) | Arginine concentration (mg/L) |
|---|---|---|---|---|
| CJ3P | 75.5 | 50 | 3.4 | 53.4 |
| CJ3P::PgapA-Sat | 69.7 | 50 | 4.5 | 78.2 |

As shown in Table 7, the CJ3P::PgapA-Sat strain showed the increased amino acid productivity compared to the control strain CJ3P.

From the above description, those skilled in the art to which the present application pertains will understand that the present application may be implemented in other specific forms without changing the technical spirit or essential characteristics thereof. In this regard, it should be understood that the examples described above are illustrative in all aspects and not restrictive. The scope of the present application should be construed as including all changed or modified forms derived from the meaning and scope of claims described below and equivalent concepts thereof rather than the above detailed description.

ACCESSION NUMBER

Name of Depository Authority: Korean Culture Center of Microorganisms (KCCM)

Accession number: KCCM12828BP

Date of Deposit: 20201029

The invention claimed is:

1. A Genus *Corynebacterium* microorganism, expressing a membrane protein with L-lysine or L-arginine exporting ability comprising the amino acid sequence of SEQ ID NO: 1, wherein the Genus *Corynebacterium* microorganism has an increased productivity of L-lysine or L-arginine.

2. The Genus *Corynebacterium* microorganism according to claim 1, wherein the Genus *Corynebacterium* microorganism comprises a polynucleotide encoding the membrane protein comprising the amino acid sequence of SEQ ID NO: 1.

3. The Genus *Corynebacterium* microorganism according to claim 2, wherein said polynucleotide is represented by the nucleotide sequence of SEQ ID NO: 2.

4. The Genus *Corynebacterium* microorganism according to claim 1, wherein the Genus *Corynebacterium* microorganism is *Corynebacterium glutamicum*.

5. A method for producing an L-amino acid, comprising culturing the Genus *Corynebacterium* microorganism according to claim 1 in a medium, and recovering the L-amino acid from the cultured microorganism, the medium, or both, and wherein the L-amino acid is L-lysine or L-arginine.

* * * * *